(12) United States Patent
Woehr et al.

(10) Patent No.: US 9,474,880 B2
(45) Date of Patent: Oct. 25, 2016

(54) SAFETY DEVICE FOR A HOLLOW MEDICAL NEEDLE

(75) Inventors: Kevin Woehr, Felsberg (DE); Hermann Riesenberger, Bebra (DE); Meinrad Lugan, Baunatal (DE)

(73) Assignee: B. Braun Melsungen AG, Melsungen (DE)

( * ) Notice: Subject to any disclaimer, the term of this patent is extended or adjusted under 35 U.S.C. 154(b) by 1064 days.

(21) Appl. No.: 13/257,572

(22) PCT Filed: May 5, 2010

(86) PCT No.: PCT/EP2010/002757
§ 371 (c)(1),
(2), (4) Date: Sep. 19, 2011

(87) PCT Pub. No.: WO2010/127846
PCT Pub. Date: Nov. 11, 2010

(65) Prior Publication Data
US 2012/0046620 A1    Feb. 23, 2012

(30) Foreign Application Priority Data

May 6, 2009  (DE) .......................... 10 2009 020 061

(51) Int. Cl.
*A61M 25/06*  (2006.01)
*A61M 5/32*  (2006.01)

(52) U.S. Cl.
CPC ........ *A61M 25/0618* (2013.01); *A61M 5/3273* (2013.01); *A61M 2005/325* (2013.01); *Y10T 29/49826* (2015.01)

(58) Field of Classification Search
CPC ................. A61M 2005/325; A61M 25/0618; A61M 5/3273; A61M 25/0606; Y10T 29/49826
USPC ................... 604/164.08, 192, 197, 263, 181
See application file for complete search history.

(56) References Cited

U.S. PATENT DOCUMENTS

| 2002/0169418 | A1* | 11/2002 | Menzi | A61M 25/0637 604/164.07 |
| 2004/0243061 | A1* | 12/2004 | McGurk | A61M 25/0618 604/164.08 |

(Continued)

FOREIGN PATENT DOCUMENTS

| CN | 1267226 A | 9/2000 |
| CN | 1917913 A | 2/2007 |

(Continued)

OTHER PUBLICATIONS

International Search Report completed Jul. 26, 2010 and mailed Jul. 30, 2010 from corresponding International Application No. PCT/EP2010/002757 filed May 5, 2010 (6 pages).

(Continued)

*Primary Examiner* — Emily Schmidt
*Assistant Examiner* — Lauren M Peng
(74) *Attorney, Agent, or Firm* — Klein, O'Neill & Singh, LLP

(57) ABSTRACT

The present disclosure relates to a set for producing a threaded connection, comprising a first and a second tubular component with an axis of revolution, one of their ends being provided with a threaded zone formed on the external or internal peripheral surface of the component depending on whether the threaded end is of the male or female type, said ends finishing in a terminal surface which is oriented radially with respect to the axis of revolution of the tubular components, a thread crest, a thread root, a load flank and a stabbing flank, the width of the thread crests of each tubular component reducing in the direction of the terminal surface of the tubular component under consideration, while the width of the thread roots increases, characterized in that the lead of the male stabbing flanks and/or load flanks is different from the lead of the female stabbing flanks and/or load flanks. The present method, system and device also pertain to a threaded connection.

30 Claims, 12 Drawing Sheets

(56) References Cited

U.S. PATENT DOCUMENTS

| | | | |
|---|---|---|---|
| 2006/0155245 A1* | 7/2006 | Woehr | A61M 25/0618 604/164.08 |
| 2008/0097343 A1* | 4/2008 | Woehr | A61M 5/3273 604/263 |
| 2012/0046620 A1 | 2/2012 | Woehr et al. | |

FOREIGN PATENT DOCUMENTS

| | | |
|---|---|---|
| EP | 1 297 859 A2 | 4/2003 |
| JP | H07-265424 | 10/1995 |
| JP | 2002-085558 A | 3/2002 |
| JP | 2003-265615 A | 9/2003 |
| JP | 2005-529717 A | 10/2005 |
| JP | 2007-136246 A | 6/2007 |
| JP | 2008-149158 A | 7/2008 |
| TW | I250880 | 3/2006 |
| WO | WO 99/08742 A1 | 2/1999 |
| WO | WO 2004/000408 A1 | 12/2003 |
| WO | WO 2004/093961 A1 | 11/2004 |
| WO | WO 2008/014908 A1 | 2/2008 |

OTHER PUBLICATIONS

Written Opinion completed Jul. 26, 2010 and mailed Jul. 30, 2010 from corresponding International Application No. PCT/EP2010/002757 filed May 5, 2010 (7 pages).

Office Action dated Aug. 8, 2013 from related Japanese Application No. 2012-508945 (7 pages).

Examiner's Report on corresponding foreign application (JP Application No. 2014-204235) from the Japanese Intellectual Property Office dated Sep. 29, 2015.

Examiner's Report on corresponding foreign application (CN Application No. 201410149811.8) from the State Intellectual Property Office of PRC dated Oct. 28, 2015.

Examiner's Report on corresponding foreign application (TW Application No. 099114310) from the Taiwan Intellectual Property Office dated Nov. 24, 2015.

* cited by examiner

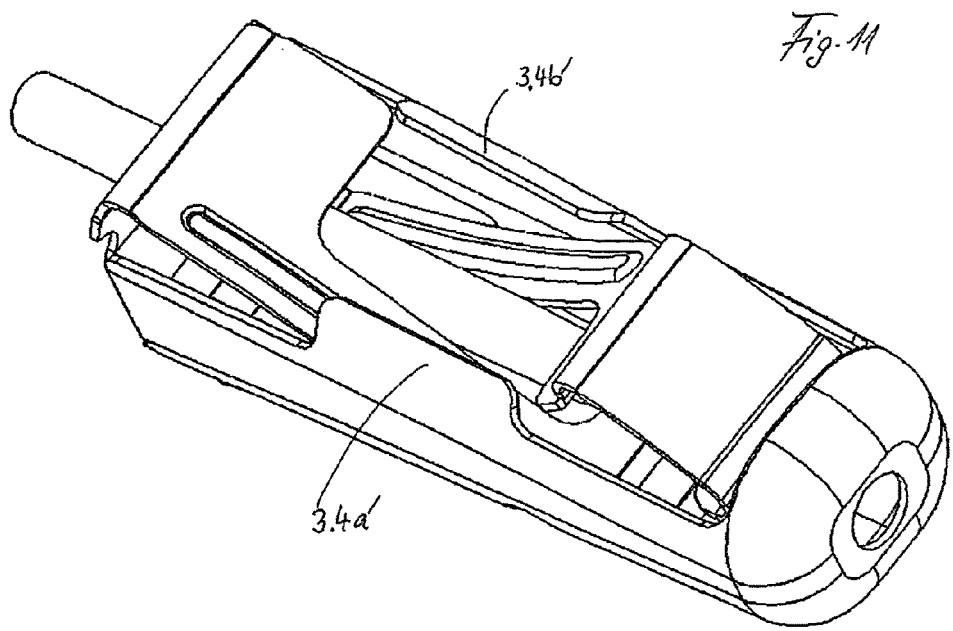

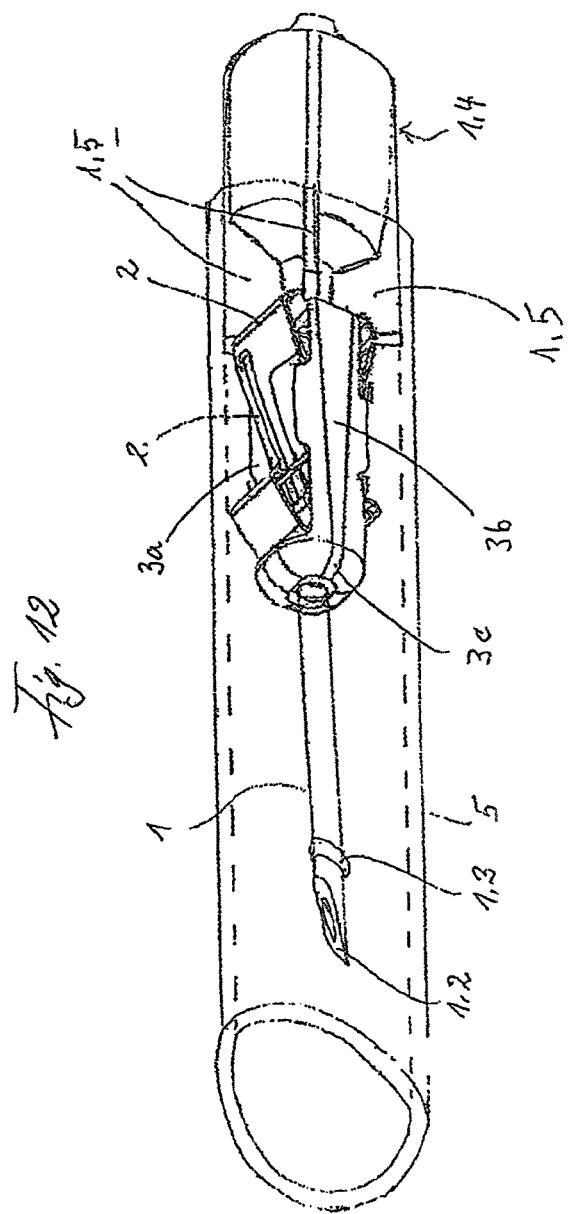

SAFETY DEVICE FOR A HOLLOW MEDICAL NEEDLE

CROSS-REFERENCE TO RELATED APPLICATIONS

This is a national phase application under 35 U.S.C. §371 of PCT Application No. PCT/EP2010/002757, filed May 5, 2010, which claims the benefit of German application No. 10 2009 020 061.4 filed May 6, 2009, the contents of which are expressly incorporated herein by reference.

FIELD OF ART

The present disclosure relates to a needle safety device.

BACKGROUND

A needle safety device of this kind is known from WO 99/08742 and EP 1 363 690, wherein a clip made of sheet metal is provided as a needle safety element in which two resilient arms extend from the proximal rear wall in a distal direction and intersect. In the ready position, bent distal ends of the arms, which are opposite each other, abut on the needle shaft, and in the protective position they cover the needle tip. Such a needle safety element can be used in connection with a catheter, as known from WO 99/08742, wherein the needle safety element is held in the catheter hub until the needle is displaced so far out of the catheter that a radial projection on the needle shaft engages with the proximal rear wall of the needle safety element, whereupon the needle safety element is withdrawn from the catheter hub with the needle. Likewise, this known needle safety element can also be used without a catheter device, as shown for example in EP 1 363 690. Additionally, from EP 1 363 690, the combination of the needle safety element with a sleeve is known. In the protective position, the proximal rear wall engages the radial projection of the needle shaft via the sleeve.

As the needle shaft extends between the intersecting arms of the needle safety element, the arms are formed relatively narrow in the middle portion. In the protective position, in which the needle safety element is positioned freely at the needle tip and the arms are no longer guided through the needle shaft, a lateral displacement of the arms of the needle safety element can occur during handling.

SUMMARY

It is an object of the present method, system and device to provide a needle safety element of the type described above such that its protective function is improved and it has a more stable structure.

According to the present method, system and device, stays extend laterally from the two arms of the needle safety element approximately parallel to the needle shaft, wherein the stays are joined at the proximal end to the proximal rear wall and to each other at the distal ends by a bracket extending transversely to the needle axis. In this way, a stiffening of the needle safety element results in which the arms of the needle safety element are prevented by the lateral stays from moving away laterally from the needle.

Preferably, the bracket can be provided at the distal ends of the stays at least on one side with a shoulder for forming a cap shape, for achieving further stiffening in the distal end area.

Additionally, the edge of the shoulder can have an extension in the proximal direction at least on one side, for limiting radial displacement of one of the arms, wherein this extension further contributes to stiffening of the structure.

For stiffening a lateral stay, at least one of the stays can be provided on at least one side with an enlargement.

Hereby, a lug extending in the peripheral direction can be formed at least on one side of at least one of the stays in the middle portion of the stay, for stiffening the stay.

When a safety element is provided that has radially protruding portions at the proximal and distal ends, the lugs expediently extend in the peripheral direction into the free region between the radially protruding portions of the needle safety element, so as not to enlarge the contours of the needle safety element in a front view of the safety element.

For joining the lateral stays to the proximal rear wall of the needle safety element, lugs can be provided at the lateral stays or at the proximal rear wall. It is also possible to provide at least one stay integral with the proximal rear wall.

Expediently, the frame formed by the lateral stays, the bracket at the distal end and the proximal rear wall, which frame is located around the movable arms of the safety element, is formed from a thin metal sheet by punching and bending; however, it is also possible to assemble a plurality of parts to obtain such a configuration.

Advantageously, a needle safety element having intersecting arms is used; however, a needle safety element can also be surrounded by a frame whose two arms do not intersect and extend on opposite sides of the needle shaft along the same.

A contribution to the stiffening of the stays is for these to have a bent cross-section or edges bent inwards. Additionally or alternatively, the stays can be provided with stiffening ribs extending longitudinally.

For engagement of the needle shaft with the proximal rear wall, crimping of the needle shaft with at least one resulting radially protruding bulge or another radial protrusion attached to the needle shaft, for example a bead, can be provided, wherein a sleeve can also be provided at the needle shaft between proximal rear wall and radial protrusion. Here, the sleeve can either be fixedly connected to the needle safety element and thus formed as part of the needle safety element, or alternatively it is not fixedly connected to the needle safety element and is merely arranged loosely on the needle at the needle shaft between needle safety element and radial protrusion. Here, in the protective position, the edge of the opening in the proximal rear wall of the needle safety element engages the radial protrusion at the needle shaft via the sleeve.

In the case of a needle shaft without a radial projection, the opening in the proximal rear wall of the needle safety element or the sleeve fixed thereto can engage with the needle shaft in the protective position by clamping when the safety element is canted or tilted in relation to the needle shaft. The needle safety element is then preferably formed with further suitable clamping areas, which engage with the needle shaft to provide additional clamping in the protective position. Even when the needle shaft has a radial protrusion, the needle safety element can also have corresponding clamping areas. For increasing the secure grip in the protective position, in a clamping embodiment an additional tether can be provided between needle safety element and needle hub.

Expediently, the bracket of the frame is provided with a bore for receiving the needle in the ready position; however, the bracket can also be formed such that it has only an approximately semicircular recess along an edge, in which recess the needle is guided.

An aspect of the present disclosure refers to a needle safety assembly comprising:
- a needle safety element slidably mounted on a needle shaft having a needle tip; the needle safety element comprising a proximal wall having an opening and a movable distal wall;
- a frame surrounding, at least in part, the needle safety element comprising a first stay and a second stay connected to a bracket and to the needle safety element.

In such an embodiment the needle safety assembly can comprise further:
- a first lug connected to the first stay along a first axial position on the first stay and extends radially relative to the needle shaft.

Further the needle safety assembly can comprise:
- a second lug connected to the second stay along a first axial position on the second stay and extends radially relative to the needle shaft.

In such an embodiment the first axial position on the first stay can be located, relative to the needle shaft, at a different position than the first axial position on the second stay.

Preferably the first lug extends radially so that an end edge of the first lug is closer to the second stay than the first stay.

Further the bracket and the two stays are unitarily formed preferably.

It is of advantage that safety element comprises a first arm and a second arm.

The present method, system and device also comprise combinations of the features described.

Further aims, advantages, features and application options of the present method, system and device follow from the following description of the embodiments with reference to the drawing. Hereby, all the features described and/or represented by the drawing form the subject matter of the present method, system and device in themselves or in any meaningful combination, independently of their summary in the claims and the back-references thereof.

BRIEF DESCRIPTION OF THE FIGURES

The present method, system and device are explained in more detail below with reference to the drawing, in which:

FIG. 11 shows a view of the embodiment in FIG. 10 from below, and FIG. 12 shows a perspective view of the needle safety device inside a protective needle cap.

DETAILED DESCRIPTION

Figure 1:
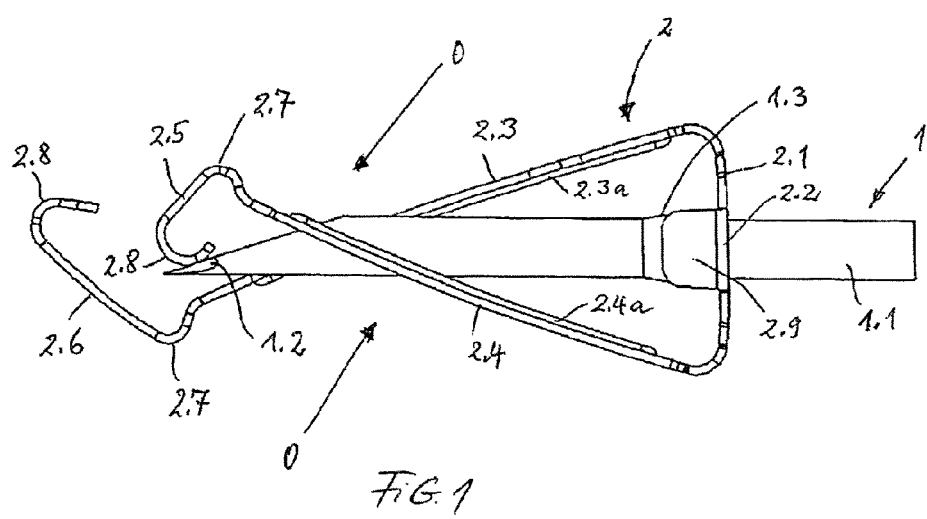
FIG. 1 shows a side view of a needle safety element having two intersecting arms in the protective position without lateral stays.

FIG. 1 shows a hollow medical needle 1. The medical needle 1 comprises a shaft 1.1 having a portion 1.3 near the needle tip 1.2 having an enlarged diameter in relation to the diameter of needle shaft 1.1, for forming a radial projection. In the embodiment according to FIG. 1, this portion 1.3 has the form of a crimp of the needle shaft, which is indented on two sides and broadened in the transverse direction. According to another embodiment, the portion 1.3 can also only have the form of a bead on the needle shaft, having a predetermined distance from the needle tip in accordance with the length of the arms of the safety element 2. A further embodiment of the portion 1.3 can also be only a bulge or a crimp on only one side of the needle shaft 1.1, or be formed by a metallic coating on the needle shaft.

On the needle shaft 1.1, there is arranged a needle safety element 2 formed from thin sheet metal, which has a proximal rear wall 2.1 having a bore 2.2, through which the needle shaft 1.1 extends displaceably. The diameter of the bore 2.2 is smaller than the outer diameter of the portion 1.3 on the needle shaft, so the needle safety element 2 cannot be displaced beyond the needle tip in the distal direction, because the edge of the bore 2.2 in the rear wall of the needle safety element retains the portion 1.3 with an enlarged diameter. Thus the bore 2.2 in the rear wall 2.1 of the needle safety element forms an engagement means with the needle shaft. Instead of a bore, a sleeve can also be provided at or in front of the proximal rear wall 2.1 of the needle safety element 2, through which sleeve the needle shaft 1.1 extends and whose inner diameter is smaller than the outer diameter of portion 1.3 having the enlarged diameter, so that by means of the sleeve, the place of engagement of needle 1 and safety element 2 in FIG. 1 is displaced to the left or in the distal direction.

In the embodiment of the needle safety element 2 in FIG. 1, two resilient arms 2.3 and 2.4 extend from the proximal rear wall in a distal direction, wherein the arms are preferably of different length and intersect in the middle portion. Bent wall portions 2.5 and 2.6 are provided at the distal ends and are formed onto the straight portions of the arms 2.3 and 2.4 by means of an elbow-shaped portion 2.7 which is bent outward. These elbow-shaped portions 2.7 serve for engagement with a catheter hub when the needle safety device is used in connection with a catheter device. At the free ends, the two arms 2.3 and 2.4 each have a bent end portion 2.8, which abuts resilientably on the needle shaft 1.1 in the ready position, and contributes to a reduction in friction by means of the bend.

Although the needle safety element 2 is shown formed from a single sheet of spring steel, it is also possible to assemble different parts of the needle safety element to give a needle safety element by welding, brazing or beading. Here, different materials can also be used for individual parts, for example plastic and metal.

FIG. 1 shows the protective position of the needle safety element 2 wherein the portion 1.3 having an enlarged diameter which can be formed as a radial projection, abuts on the edge of the bore 2.2 in the proximal rear wall 2.1. The longer arm 2.3 overlaps the needle tip 1.2 by means of the wall portion 2.6. The distance between needle tip 1.2 and portion 1.3 can also be configured smaller, so that the shorter arm 2.4 also overlaps the needle tip.

Figure 2:
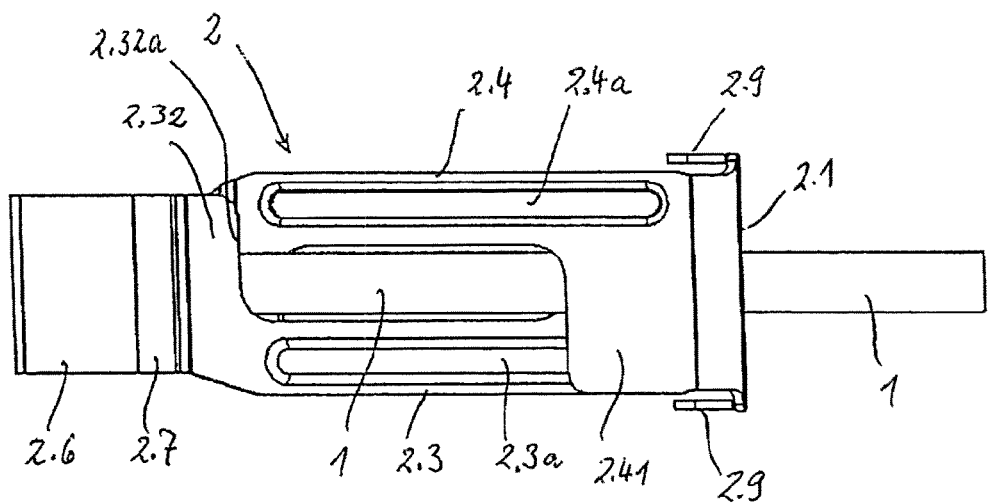
FIG. 2 shows a view of the needle safety element from below in FIG. 1.

As FIG. 2 shows at 2.41, the arms 2.3 and 2.4 adjacent to the proximal rear wall 2.1 have a widened portion which merges into a narrow portion along which a stiffening rib 2.3a or 2.4a is formed. The needle 1 extends between these two narrower, intersecting, laterally distanced portions. In the distal end portion, the arms 2.3 and 2.4 again have widened portions, as FIG. 2 shows at 2.32, wherein the distal wall portions 2.5 and 2.6 have a lesser width dimension than the arms 2.3 and 2.4 in the proximal area adjacent to the rear wall 2.1.

Figure 3:
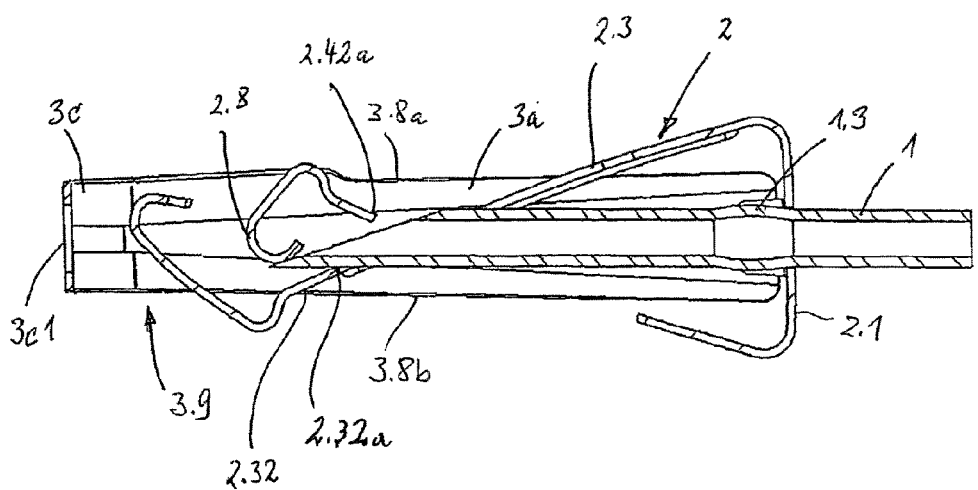
FIG. 3 shows a longitudinal section through the needle safety element in the protective position with a lateral stay.

As shown in FIGS. 1 and 3, the bent end portion 2.8 of the arm 2.4 abuts laterally on the needle tip 1.2, so that the safety element 2 cannot be tilted in the counter-clockwise direction relative to the needle shaft in FIGS. 1 and 3. To prevent tilting of the safety element 2 in the clockwise direction relative to the needle shaft in the protective position, the transversely-extending edge 2.32a (FIGS. 2 and 3) of the widened portion 2.32 adjacent to the elbow-shaped portion 2.7 is positioned in such a way that this edge 2.32a abuts on the needle in the protective position of FIGS. 1 to 3. If the distal end of the arm 2.4 also covers the needle tip 1.2 in the protective position, then the corresponding edge 2.42a (FIG. 3) of the widened portion adjacent to the elbow-shaped portion 2.7 can also be used for preventing tilting of the safety element 2 in relation to the needle shaft.

In the proximal area of the needle safety element 2, lateral stays 3a and 3b (FIG. 8) are fixed, which extend along both sides of the arms 2.3 and 2.4. In the embodiments shown, bent and protruding lugs 2.9 (FIGS. 1 and 2) are formed at the proximal rear wall 2.1 in the distal direction, wherein the proximal ends of the stays 3a and 3b are fixed onto these lugs 2.9 by adhesion, laser welding or resistance welding such that they form a unit with the safety element 2. Instead of the lugs 2.9, corresponding lugs can also be formed on the proximal ends of the stays which can be joined to the proximal rear wall 2.1 of the needle safety element after bending.

Thus the present method, system and device comprise a needle safety element having preferably two intersecting arms having two stays which are spaced apart from each other and are fixedly joined to the proximal end of the needle safety element. In one embodiment, the fixing location is distal of the proximal wall by means of lugs extending from the proximal wall in a distal direction. In another embodiment, the fixing at the proximal wall takes place by bending over the two proximal ends of the two stays and fixing the bent ends directly at the proximal wall.

According to another embodiment, at least one of the stays 3a and 3b can be formed by means of punching of a sheet metal integral with the proximal rear wall of the safety element 2.

The stays 3a, 3b likewise preferably consist of sheet metal, and they are joined to each other at the distal ends by a bracket 3c, which extends transverse to the needle 1 and is preferably provided with a throughbore 3c1 for receiving the needle 1. The stays 3a and 3b each have upper and lower edges 3.8a and 3.8b (FIG. 3), so the two intersecting arms 2.3 and 2.4 are more visible with respect to their function.

The bracket 3c with the two lateral stays 3a and 3b, which can be denoted as a protective band or frame 3.9 in FIG. 3, prevents lateral displacement of the needle safety element 2 relative to the needle shaft 1. As can be seen in FIG. 1, the safety element 2 can become displaced on the needle section 1.3, so the distal wall areas 2.5 and 2.6 can move out of the protective position somewhat, i.e. somewhat out of the plane of FIG. 1. By means of the two spaced-apart lateral stays 3a and 3b, a relative movement between needle tip 1.2 and distal wall portions 2.5 and 2.6 is prevented—if such a relative movement occurs at all—because the needle 1 is fenced in the space defined by the two stays and the two arms. Because the longer arm 2.3 cannot be displaced laterally or downward, the possibility of the needle tip becoming exposed by a lateral movement is prevented, as the protective element 2 is moved into the protective position. Thus the present method, system and device comprise a protective element having two intersecting arms and a protective band or frame which has two spaced-apart stays joined to the protective element in the proximal area and joined to the bracket in the distal area, for preventing deflection of the two stays against each other or away from each other. The joining of the two stays also limits the displacement of the safety element by limiting the movement of the needle tip to an area which is defined by the two stays and the two arms, called a needle containment space. In certain embodiments, the arms can be generally parallel or intersect as shown.

To stiffen the stays 3a, 3b formed from a metal strip, stiffening ribs 3a1 and 3b1 are formed along these in the wall areas. Alternatively or additionally to this, the metal strip of the stays can be formed from a thicker sheet material. In a cross-sectional view, the stays 3a, 3b themselves can be slightly bent or have edges bent inward so that the stiffness of these stays is improved. In the cross-sectional view, the flat extension of the stays 3a, 3b extends transverse to the flat extension of the arms 2.3 and 2.4, as shown in FIG. 3.

In a plan view of the embodiment in FIG. 3, the bracket 3c forms an approximately rectangular frame with the proximal rear wall 2.1 of the needle safety element and the two stays 3a and 3b, wherein the two arms 2.3 and 2.4 of the needle safety element are able to move inside this frame. Thus according to an aspect of the present method, system and device a frame is provided comprising a distal wall (bracket), two stays and a proximal wall within which the two intersecting arms can move. The safety element is also to be understood as such, having two arms which can lie in a position radially outside the space or region delimited by the frame, and moving into the region delimited by the frame. According to one embodiment, the safety element can have two arms which start from a position outside the region delimited by the frame and intersect in a position inside the region delimited by the frame.

Figure 4:
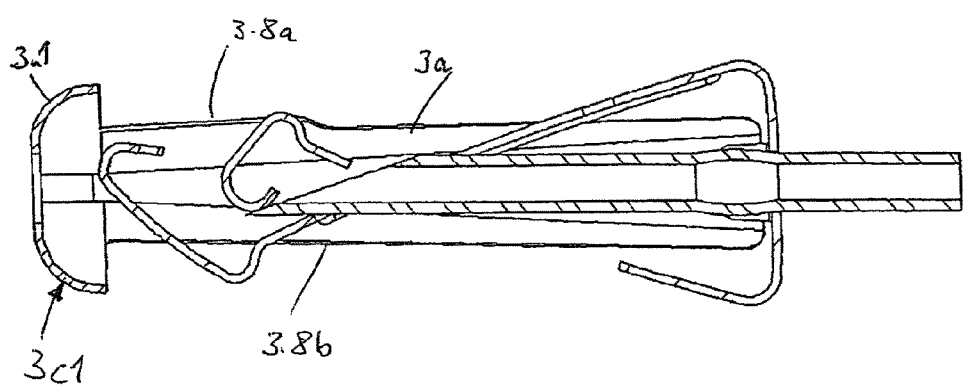
FIG. 4 shows in the same view as FIG. 3 an embodiment with a cap-shaped bracket.

FIG. 4 shows an embodiment in which the distal bracket 3c1 is formed on the upper and lower side by a rounded boss 3.1 in the form of a cap. The rounded cap is preferably provided for avoiding sharp edges. This rounded boss 3.1 can also be formed on only one side of the bracket 3c1. As shown, the two rounded bosses are arranged above and below the two edges 3.8a and 3.8b of the two band-shaped stays. If only one rounded boss is provided, then a device is understood thereby which has a single boss either above or below the two edges and a straight edge on the other side of the bracket.

Figure 5:
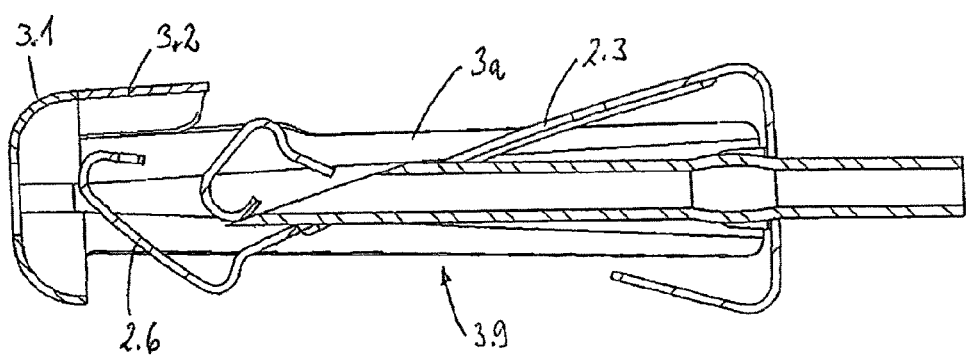
FIG. 5 shows an embodiment with a cap extended on one side.

In the embodiment according to FIG. 5, the boss 3.1 is provided with an extension 3.2 in the proximal direction on the side opposite the distal end of the longer arm 2.3, and by means of this extension a displacing movement of the distal end 2.6 of the longer arm is further prevented. For example, when the distal end 2.6 moves upwards in FIG. 5, it will come to abut on the elongation 3.2 and thus it will be prevented by this elongation from moving out too far radially from the space or region defined by the frame. On the other hand, this elongation 3.2, corresponding in cross-section to the rounded boss 3.1, is configured with regard to its length such that the short arm in FIG. 5 can move out upwardly over this elongation 3.2.

Figure 6:
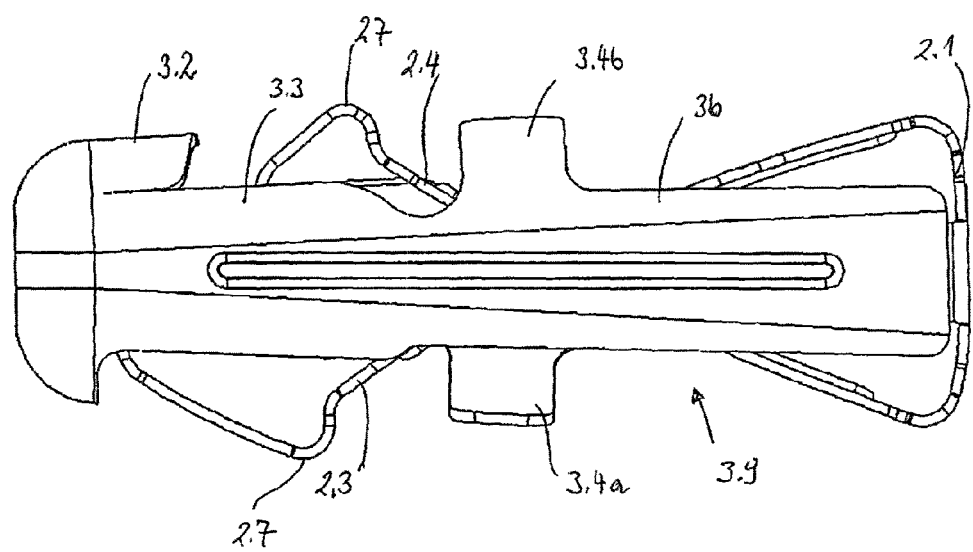
FIG. 6 shows an embodiment with a lug on one side of each stay, wherein the arms are in the ready position.
Figure 7:
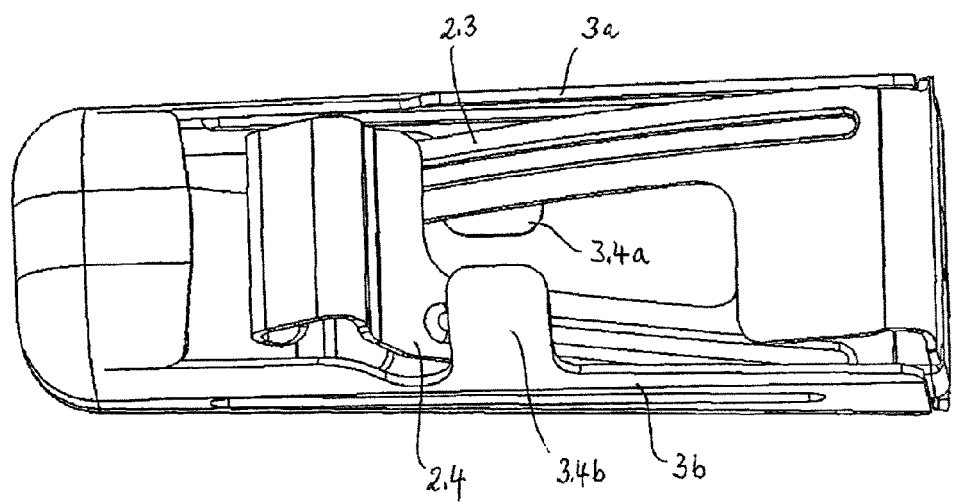
FIG. 7 shows a plan view from above in FIG. 6.

FIGS. 6 and 7 show an embodiment in which the stays made from a metal sheet by punching and/or stamping have an enlargement 3.3 on at least one side in the distal end portion. The enlargement is preferably formed on the side of the distal end of the shorter arm 2.4 and ensures improved protection from lateral displacement especially of the distal end of the shorter arm, wherein the proximal elongation 3.2 of the boss 3.1 at the side edges abuts on this enlargement 3.3 as shown in FIG. 6.

Depending on the type of cutting die, during production of the guard band or stiffening bracket forming a frame with the rear wall 2.1, the distal end portion of the enlargement 3.3 can extend into the proximal elongation 3.2 at the cap-shaped bracket. For example, the extension 3.2 can extend somewhat upwards such that at least a part of this extension 3.2 is covered by the enlargement 3.3 in a perspective view of FIG. 6. This proximal elongation 3.2 can have in the middle portion thereof a gap or a parting line in the axial direction of the needle, which parting line is determined by the metal blank which is used for deformation after punching by stamping and bending.

Approximately in the area of the point of intersection of the two arms 2.3 and 2.4 of the needle safety element, on one side of each stay a lug 3.4a and 3.4b is formed extending in the peripheral direction, bent somewhat inwardly toward the needle and adapted to the curve of the elongation 3.2 in the cap portion. The lug 3.4b is formed on the side of the stay 3b on which the shorter arm 2.4 extends, as shown in the plan view in FIG. 7, so that this lug 3.4b ensures further protection from upward displacement of the arm 2.4 in FIGS. 6 and 7. In a corresponding way, the lug 3.4a is formed at the lower side of the stay 3a in FIGS. 6 and 7, to prevent the arm 2.3 extending along the stay 3a from downward displacement.

Thus an aspect of the present method, system and device is a protective element having two arms, wherein each arm comprises a portion extending along an associated side of the needle shaft. A band or a stay also extends on each side of the needle shaft and of the two arms. In one embodiment, a lug extending in the peripheral direction extends from each stay over an associated arm. According to a further aspect of the present method, system and device, a protective band or frame is provided which surrounds a safety element, wherein two spaced-apart lugs are provided which each extend from a stay, and wherein the two lugs extend in the clockwise direction in the view from the proximal to the distal end.

Figure 8:
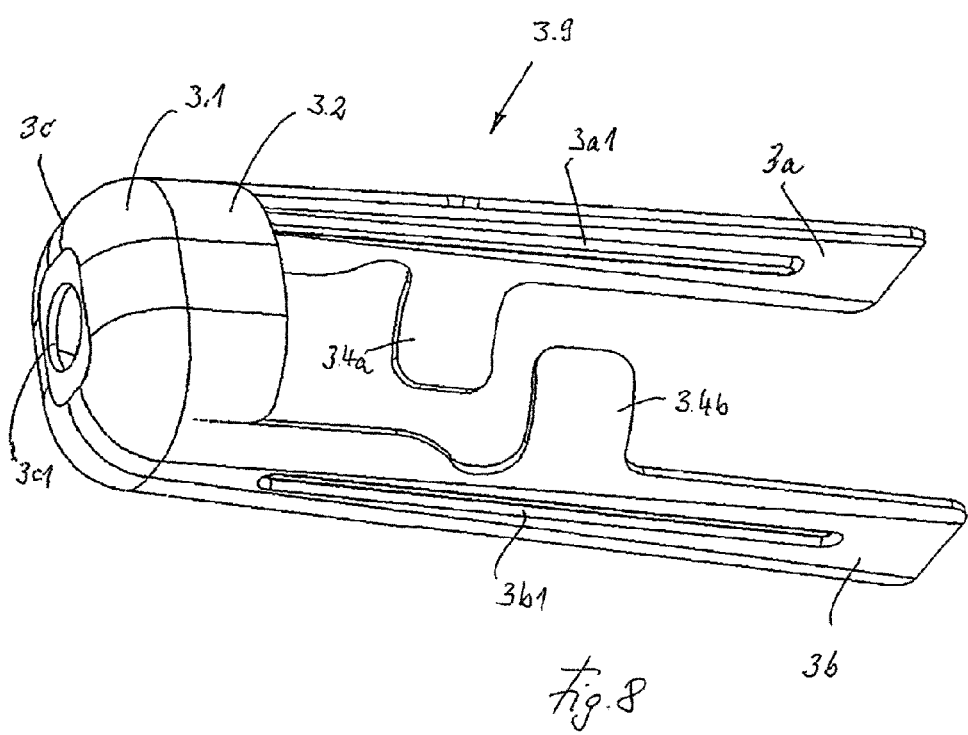
FIG. 8 shows a perspective view of the bracket shape in FIGS. 6 and 7 without the needle safety element.
Figure 9:
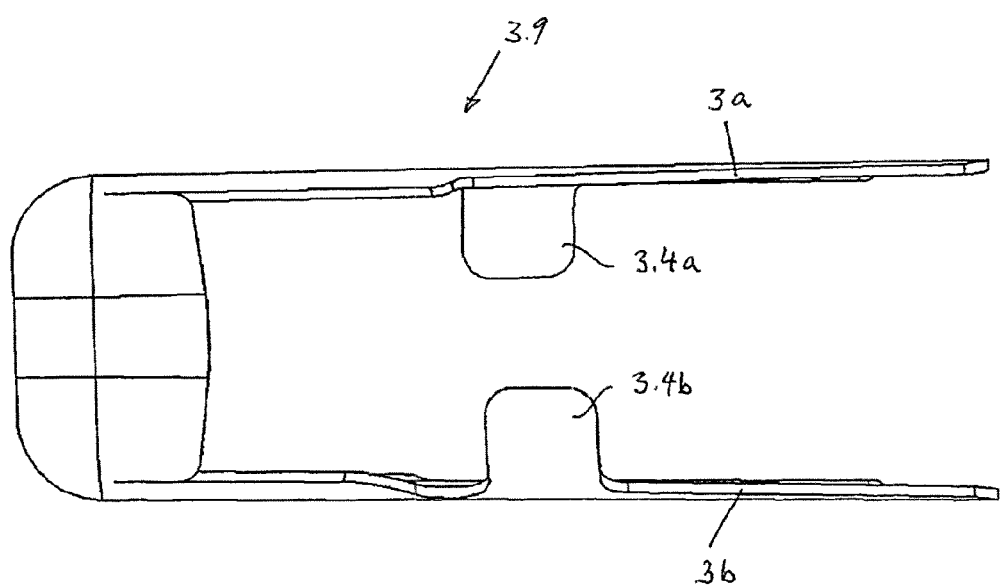
FIG. 9 shows a plan view of the embodiment according to FIG. 8.

While FIG. 5 shows the arms 2.3 and 2.4 in the protective position, the arms in FIG. 6 are shown in the ready position, in which the bent end portions 2.8 of the arms abut on the needle shaft which is not shown in FIG. 6. In this position, the elbow-shaped portions 2.7 project further upwardly and downwardly over the lateral stays 3a and 3b, so that the lugs 3.4a and 3.4b offer additional protection from displacement of the arms. FIGS. 8 and 9 show the arrangement of the lugs 3.4a and 3.4b at the stays without a safety element. In other words, FIGS. 8 and 9 show a band-shaped guard 3.9 provided according to an aspect of the present method, system and device, wherein the safety element 2 is not shown in FIGS. 8 and 9.

Figure 10:
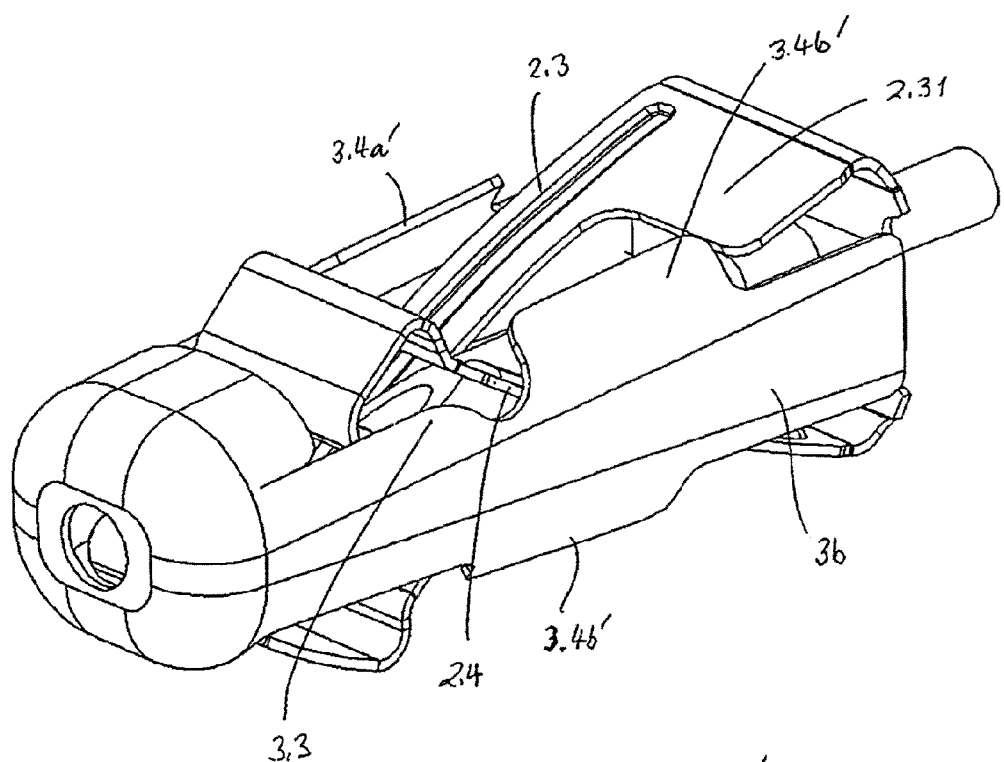
FIG. 10 shows a perspective view of a further embodiment in the protective position.

FIG. 10 is a perspective view of an embodiment in which lugs 3.4a' and 3.4b' are formed enlarged in the longitudinal direction of the stays, by means of which the protection from deformation of the needle safety element 2 is further improved. Here, a contribution to the stiffness of the device is also made by a lug being formed on each side of each stay 3a and 3b, as shown in FIGS. 10 and 11, wherein FIG. 11 represents a view of the needle safety device from below in FIG. 10. In other words, each stay comprises two lugs extending from each longitudinal edge of the stay. As can be seen from FIG. 10, due to the enlargement of the lug, in the proximal direction a shorter distance results between the proximal edge of the lug 3.4b' and the widened portion 2.31 of the arm 2.3, while on the opposite side, the distal edge of the enlarged lug 3.4b' lies in the distal direction a shorter distance from the arm 2.4 and overlaps the same, so that the two arms 2.3 and 2.4 can be displaced upwardly and downwardly to a slighter degree than in the embodiment of FIGS. 6 and 7.

Thus the present method, system and device comprise an elongation or extension of the lug in a distal and/or proximal direction at the associated stay, to limit upward and downward displacement of the arm. In other words, the lugs can be configured in the axial direction such that they determine the displacement of the arms in the radial direction.

To achieve this effect, the lugs formed at the opposite stays 3a and 3b can also be offset to each other in the longitudinal direction, so that for example in FIG. 10 the lug 3.4b' is offset further in the distal direction relative to the opposite lug 3.4a'. FIG. 11 shows lugs 3.4a' and 3.4b' offset relative to each other in the longitudinal direction.

The lugs have rounded corners to avoid sharp edges. Preferably, an arc-shaped transition is formed between the enlargement 3.3 and the shoulder of the lug 3.4b', as FIG. 10 clearly shows.

Thus a further aspect of the present method, system and device is a safety means having a band-shaped guard having two lugs along a first side which are offset in the axial direction, and along a second side, which are also offset in the axial direction.

The stiffening frame made from thin sheet metal by punching and bending and having the stays 3a, 3b, has an approximately U-shaped basic form with flattened shoulders corresponding to the stays, as can be seen from FIGS. 8 and 9. The stays 3a and 3b provided with lugs, extending transverse to the arms 2.3 and 2.4, extend continuously from the proximal end over the distal end of the needle safety element 2 and provide a stiff frame for the needle safety device.

According to another embodiment, the lugs 3.4a' and 3.4b' in FIGS. 10 and 11 can be formed lengthened in the peripheral direction, so that the edges of the lugs, which lie opposite each other, form a narrow gap on the upper and lower side of the needle safety device, which gap is formed relatively wide in FIGS. 10 and 11 by the distance of the opposite edges of the lugs 3.4a' and 3.4b'. In other words, the edge of each lug extending in the longitudinal direction can extend further in the direction towards the needle shaft or in the peripheral direction, so a narrower gap is present between the two opposite edges of the two lugs 3.4a' and 3.4b' extending in the longitudinal direction in FIG. 11.

According to a further embodiment, the opposite lugs 3.4a' and 3.4b' can also be lengthened in the peripheral direction so far that their edges abut at each other on the upper and lower side or only on one side and thus overlap or cover the middle portion of the intersecting arms 2.3 and 2.4. In such an embodiment, the lugs 3.4a and 3.4b provide a closed or approximately closed cross section together with the stays 3a and 3b in a sectional view of the needle safety device. Hereby, the lugs surrounding the needle safety element 2 extend into the free space O (FIG. 1) between the proximal and the distal ends of the needle safety element such that they lie inside the elbow-shaped portions 2.7 of the arms of the safety element in a front view of the needle safety element, at least when the arms are in the ready position, in which they are prestressed in a radially outward direction by the needle shaft, as shown in FIG. 6. The peripheral line of the elongation 3.2 is also formed together with the cap-shaped bracket such that it lies radially inside the elbow-shaped portions 2.7 of the arms in the ready position, as shown in FIG. 6. In this way, the radial outer dimensions in the area of the cap and of the lugs correspond approximately to the outer dimension of the proximal rear wall 2.1. Preferably, the cap and the lugs have a smaller profile than the proximal rear wall 2.1 in the front view from the left in FIG. 6.

In the embodiment of FIG. 6, each lug 3.4a and 3.4b can also extend along approximately half of the periphery up to the opposite stay 3a or 3b, so that in this way too, a closed cross section is provided in the middle portion of the needle safety element 2.

According to a further modification, the needle safety element can also be formed with arms 2.3 and 2.4 extending approximately parallel to each other, wherein the two arms can be bent in the middle portion preferably somewhat inwardly toward the needle, so that in this area the lugs 3.4a and 3.4b can overlap the arms of the safety element further inwardly, while the elbow-shaped portions 2.7 provided for engagement with a catheter hub are exposed. In the embodiments shown, in the view according to FIG. 1, by means of the intersecting arms 2.3 and 2.4 a free space O is provided in their middle area between the articulation portion of the arms at the proximal rear wall 2.1 and elbow-shaped portions 2.7, into which the lugs 3.4a and 3.4b can extend. This free space O can also be formed by deflection of non-intersecting but opposite arms.

The needle safety element 2 described is preferably formed by punching and bending of a thin metal strip so that altogether the smallest possible overall dimensions are achieved. In practice, the safety element 2 has for example a longitudinal dimension of approximately 8 mm and a radial dimension of approximately 3 mm. In a corresponding way, the frame around the two arms is formed by punching and bending of the sheet metal such that the overall dimensions of the needle safety device are not increased by a remarkable amount. It is clear that the same configuration can be achieved using a plurality of components or parts which are assembled to obtain a safety element having a band-shaped guard for improving stability. The plurality of single parts can be formed from different metals or materials or from a plastic-metal compound.

According to a modification, the cap-shaped bracket 3c can also be joined to the stays 3a and 3b by adhesion or welding. The bracket can also be formed such that it extends under or over the needle shaft, wherein for example an approximately semicircular recess can be formed in the bracket for guiding the needle shaft in the ready position. A bracket having a bore for the passage of the needle as shown is preferred.

When the elbow-shaped portions 2.7 have another function than engaging with a catheter hub, these arc-shaped portions 2.7 can also have another shape. For example, they can be bent sharply, to form an edge acting outwardly. It is also possible to form this arc-shaped portion 2.7 flattened, so that it does not protrude or hardly protrudes over the periphery of the cap-shaped bracket 3c.

Instead of sheet metal, another material can also be used, which when having small dimensions is correspondingly formable to form a needle safety device having small dimensions in this way.

The small dimensions of the needle safety device made of sheet metal also allow the needle safety device arranged in the ready position on a hollow medical needle in the proximal area of the needle shaft to be covered by a conventional needle safety cap 5, which cap is placed on a needle hub 1.4, as FIG. 12 shows, without the risk of the needle safety device being moved on the needle shaft during removal of the needle safety cap 5.

Preferably, grooves extending lengthwise are formed onto the needle safety cap 5 and distributed over its inner periphery, and by means of these grooves the needle safety cap is held on the needle hub 1.4 on which corresponding radially projecting ribs 1.5 are formed distributed over the periphery. Due to the small radial dimensions of the needle safety element 2 having the stiffening frame 3a to 3c, there is no risk that the needle safety cap 5 could contact the needle safety element 2, so the inner and/or outer surfaces of the needle safety cap 5 can also be formed corrugated.

If the described needle safety device is made of plastic, it has larger dimensions, wherein a frame formed as described is provided in the same way around the resilient arms of the needle safety element.

Instead of two bent distal end walls of the safety element 2, a safety element can also be provided wherein only one arm has a bent distal end wall, which overlaps the needle tip in the protective position.

The invention claimed is:

1. A needle safety assembly comprising:
   a needle safety element slidably mounted in a catheter hub and on a needle shaft having a needle tip; the needle safety element comprising a proximal wall having an opening and two movable arms; the needle safety element being proximal of the needle tip in a ready position and covering the needle tip in a protective position;
   a frame surrounding, at least in part, the needle safety element comprising a first stay and a second stay having distal ends and proximal ends and connected to a bracket at the distal ends and being fixedly attached at the proximal ends; and
   wherein the frame and the needle safety element are displaced from the catheter hub in the protective position.

2. The needle safety assembly of claim 1, further comprising a first lug connected to the first stay along a first axial position on the first stay and extends radially relative to the needle shaft.

3. The needle safety assembly of claim 2, further comprising a second lug connected to the second stay along a first axial position on the second stay and extends radially relative to the needle shaft.

4. The needle safety assembly of claim 3, wherein the first axial position on the first stay is located, relative to the needle shaft, at a different position than the first axial position on the second stay.

5. The needle safety assembly of claim 2, wherein the first lug extends radially so that an end edge of the first lug is closer to the second stay than the first stay.

6. The needle safety assembly of claim 1, wherein the bracket and the two stays are unitarily formed.

7. The needle safety assembly of claim 1, wherein the two arms are attached to the proximal wall.

8. A method of forming a needle safety assembly use in a catheter hub, the method comprising:
   placing a needle safety element in sliding communication with a needle shaft having a needle tip and into a catheter hub; said safety element comprising a proximal wall having an opening and two movable arms; said safety element covering the needle tip in a protective position;

surrounding, at least in part, said needle safety element with a frame; said frame comprising a first stay and a second stay having distal ends and proximal ends and connected to a bracket at the distal ends and being fixedly attached at the proximal ends; and wherein the frame and the needle safety element are displaced from the catheter hub in the protective position.

9. The method of claim 8, wherein the bracket, the two stays, and the proximal wall define two opposed rectangular openings.

10. The method of claim 8, further comprising forming at least one lug on one of the first stay and the second stay to delimit rotation of the needle shaft relative to the frame.

11. The method of claim 10, further comprising a second lug, and wherein the at least one lug and the second lug are offset in an axial direction.

12. The method of claim 8, further comprising limiting displacement of the needle safety element by limiting movement of the needle tip to an area defined by the first stay and the second stay and two intersecting arms.

13. The method of claim 8, further comprising bending the first stay and the second stay so that bent portions of the first stay and the second stay are parallel to the proximal wall.

14. The method of claim 8, further comprising positioning the two movable arms of the needle safety element radially outside a space defined by the frame and moving the first arm and the second arm into the space defined by the frame.

15. The method of claim 8, further comprising an extension on the bracket extending in a proximal direction.

16. The method of claim 8, wherein the two movable arms are attached to the proximal wall.

17. A needle safety assembly comprising:
a needle safety element slidably mounted on a needle shaft having a needle tip, the needle safety element comprising:
a proximal wall having an opening;
a moveable distal wall; and
two movable arms which do not intersect and extend along opposite sides of the needle shaft;
a frame surrounding, at least in part, the needle safety element assembled from a first stay and a second stay connected to a bracket and the proximal wall, within which the two movable arms can move;

wherein the frame is located around the movable arms of the safety element; and wherein the stays are joined to each other at the distal ends by the bracket.

18. Needle safety assembly according to claim 17, wherein the stays extend laterally from the two arms of the needle safety element approximately parallel to the needle shaft.

19. The needle safety assembly according to claim 17, wherein the bracket extends transversely to the needle axis.

20. The needle safety assembly according to claim 17 one of the preceding claims, wherein the stays are joined at the proximal end to the proximal rear wall.

21. The needle safety assembly according to claim 17, wherein the first stay and the second stay are connected to the needle safety element.

22. The needle safety assembly according to claim 17, wherein the stays of the frame are fixedly connected at their proximal ends with the proximal wall of the needle safety element.

23. The needle safety assembly according to claim 17, further comprising protruding lugs formed on the proximal ends of the stays.

24. The needle safety assembly according to claim 17, wherein at least one stay is integral with the proximal wall.

25. The needle safety assembly according to claim 17, wherein the bracket and the stays are unitarily formed.

26. The needle safety assembly according to claim 17, wherein the frame formed around the moveable arms of the needle safety element by the lateral stays and the bracket is formed from thin sheet metal by punching and bending.

27. The needle safety assembly according to claim 17, wherein needle safety element comprises two resilient arms extending from the proximal wall in the distal direction, both arms being provided with a distal end portion opposite each other, the moveable distal wall being provided on the distal end portion of each of the resilient arms.

28. The needle safety assembly according to claim 17, wherein the distal end portions of the arms abut on the needle shaft in the ready position.

29. The needle safety assembly according to claim 27, wherein the distal end portions of the arms cover the needle tip in the protective position.

30. The needle safety assembly according to claim 17, wherein the stays have a curved cross-section or have inwardly bent edges in the sectional view.

* * * * *

UNITED STATES PATENT AND TRADEMARK OFFICE
CERTIFICATE OF CORRECTION

PATENT NO. : 9,474,880 B2
APPLICATION NO. : 13/257572
DATED : October 25, 2016
INVENTOR(S) : Kevin Woehr et al.

Page 1 of 1

It is certified that error appears in the above-identified patent and that said Letters Patent is hereby corrected as shown below:

On the Title Page

In Column 2, item (57) in "Abstract", Lines 1-17, delete "The present disclosure relates to a set for producing a threaded connection, comprising a first and a second tubular component with an axis of revolution, one of their ends being provided with a threaded zone formed on the external or internal peripheral surface of the component depending on whether the threaded end is of the male or female type, said ends finishing in a terminal surface which is oriented radially with respect to the axis of revolution of the tubular components, a thread crest, a thread root, a load flank and a stabbing flank, the width of the thread crests of each tubular component reducing in the direction of the terminal surface of the tubular component under consideration, while the width of the thread roots increases, characterized in that the lead of the male stabbing flanks and/or load flanks is different from the lead of the female stabbing flanks and/or load flanks. The present method, system and device also pertain to a threaded connection." and insert -- Method, system and device involving a needle device with a needle safety element with improved stable structure. A frame can surround the needle safety element to provide added stiffening of the needle safety element. The frame can include stays extending laterally of the needle safety element. The needle safety element with the frame can be slidably located on a needle and in a catheter hub in a ready to use position and be removable from the catheter hub in a protective position. --, therefor.

In the Specification

In Column 4, Line 51, delete "resilientally" and insert -- resiliently --, therefor.

In the Claims

In Column 12, Line 5, in Claim 18, delete "Needle" and insert -- The needle --, therefor.

Signed and Sealed this
Twenty-third Day of May, 2017

Michelle K. Lee
*Director of the United States Patent and Trademark Office*